US007731826B2

(12) United States Patent
Hibbs et al.

(10) Patent No.: US 7,731,826 B2
(45) Date of Patent: Jun. 8, 2010

(54) CONTROLLED TRANSLOCATION OF A POLYMER IN AN ELECTROLYTIC SENSING SYSTEM

(75) Inventors: Andrew D. Hibbs, La Jolla, CA (US); Eric A. Duff, San Diego, CA (US)

(73) Assignee: Electronic Bio Sciences, LLC, San Diego, CA (US)

( * ) Notice: Subject to any disclaimer, the term of this patent is extended or adjusted under 35 U.S.C. 154(b) by 347 days.

(21) Appl. No.: 11/839,793

(22) Filed: Aug. 16, 2007

(65) Prior Publication Data

US 2008/0041733 A1 Feb. 21, 2008

Related U.S. Application Data

(60) Provisional application No. 60/838,170, filed on Aug. 17, 2006.

(51) Int. Cl.
*G01N 27/26* (2006.01)
*G01N 27/28* (2006.01)

(52) U.S. Cl. ........................ 204/450; 204/547; 204/400; 204/403.01; 205/775; 435/6; 435/287.2

(58) Field of Classification Search ................. 205/775; 204/400, 403.01, 403.06, 408, 547, 450; 435/6, 287.2

See application file for complete search history.

(56) References Cited

U.S. PATENT DOCUMENTS

| 4,909,919 | A | * | 3/1990 | Morris et al. ............... 204/603 |
| 5,748,491 | A | | 5/1998 | Allison et al. |
| 6,528,258 | B1 | | 3/2003 | Russell |
| 6,673,615 | B2 | | 1/2004 | Denison et al. |
| 2003/0017483 | A1 | * | 1/2003 | Ecker et al. ..................... 435/6 |
| 2003/0057094 | A1 | * | 3/2003 | Bryning et al. ............. 204/547 |
| 2003/0099951 | A1 | | 5/2003 | Akeson et al. |
| 2004/0124084 | A1 | * | 7/2004 | Lee et al. ..................... 204/600 |
| 2004/0146849 | A1 | * | 7/2004 | Huang et al. .................... 435/4 |

OTHER PUBLICATIONS

Ying et al., "Frequency and Voltage Dependence of the Dielectrophoretic Trapping of Short Lengths of DNA and dCTP in a Nanopipette", Biophysical Journal, vol. 86, pp. 1018-1027, Feb. 2004.

* cited by examiner

*Primary Examiner*—Nam X Nguyen
*Assistant Examiner*—Jennifer Dieterle
(74) *Attorney, Agent, or Firm*—Diederiks & Whitelaw, PLC

(57) ABSTRACT

An electrolytic sensing system for measuring a blocking signal allows for controlled translocation of a molecule, such as DNA, through a fluid channel. A substantially constant electric field supplied by a DC source is applied across the fluid channel and induces translocation of the molecule within the system. An oscillating electric parameter (e.g. current or voltage) supplied by an AC source is also applied across the fluid channel as a means for measuring a blocking signal. The substantially constant electric field can be altered to provide more detailed control of the molecule and, optionally, run a select portion of the molecule through the channel multiple times to provide numerous signal readings. A temperature control stage cools the system, providing further control of molecule translocation. A modified or non-modified protein pore may be utilized in the fluid channel. The system allows for long DNA strands to be sequenced quickly without amplification.

40 Claims, 5 Drawing Sheets

CONTROLLED TRANSLOCATION OF A POLYMER IN AN ELECTROLYTIC SENSING SYSTEM

CROSS-REFERENCE TO RELATED APPLICATIONS

The present invention claims the benefit of U.S. Provisional Patent Application Ser. No. 60/838,170 entitled "Controlled Translocation of a Polymer Through a Nanopore and Means to Measure Individual Monomers" filed Aug. 17, 2006.

BACKGROUND OF THE INVENTION

1. Field of the Invention

The present invention pertains to the art of measuring the physical configuration of a molecule and, more particularly, to sequencing individual monomers of a polymer via measuring the change in ionic current that is produced by the polymer when it passes through a narrow constriction within a fluid channel.

2. Discussion of the Prior Art

There has been considerable interest in recent years in measuring the interaction kinetics of single molecules with ion channels and associated protein pores by the method of recording the momentary change in the ionic current that passes through the channel while the molecule is present. In general, the molecule partially blocks the current flow with an amplitude and duration that are characteristic of the particular physical size and configuration of the molecule, and its chemical interaction with active sites within the channel. Efforts are underway to apply this current blocking method as the basis of a sensor system that identifies the presence of individual target molecules within a background of typical environmental chemical species.

A particular application of the current blocking method is to identify individual monomers within a polymer and, in the ideal case, is sequence the individual bases of complex biological polymers such as DNA and RNA. One of the most promising methods being investigated under the Human Genome Project is to drive single stranded DNA (ssDNA) through a nanoscale channel and attempt to measure the characteristic current change through the channel for each nucleotide base. These methods have been implemented using either a naturally occurring pore, such as alpha hemolysin (aHl), suspended in a bilayer, or using nanometer scale pores in a substrate such as silicon. However, advancements with both designs have been unable to successfully, rapidly sequence DNA because the DNA translocates through the pore too quickly for the electronics to measure the rapid and small changes in current produced by each nucleotide base.

Translocation rates for single stranded polymers under 120 millivolt (mV) applied voltage at 25° C. are on the order of 100 micrometers per second (μm/sec) to 500 μm/sec, providing an average time to measure the signal corresponding to an individual monomer of DNA or RNA (i.e. localize to the spatial extent to a single base) in the order of 0.8 to 4 microseconds (μs) per base. The electric field force on the DNA is balanced by an average force produced by hydrodynamic drag and the molecular interaction with the channel, resulting in a translocation velocity that is proportional to the applied force. Thus, if the applied voltage that produces the electric field is reduced from 100 mV to 10 mV, the velocity of the polymer is reduced ten fold, giving times ranging from 8 μs to 40 μs per base. Reducing the applied voltage thereby offers a means to increase the time a given DNA base is located in the appropriate region of the pore. Increasing the available time allows a number of measurements to be made and averaged in order to improve the accuracy of the measurement. However, in conventional systems, the applied voltage also produces the current that gives the signal characteristic of the particular blocking event. This creates the conflict that if the applied voltage is reduced the current is reduced in direct proportion. Conversely, if the applied voltage is increased to produce a larger current, the DNA translocates faster, giving less time to measure the signal.

Ideally, the molecular translocation rate is reduced to a very low level to allow measurement times on the order of 1 millisecond (ms) per base. However, as the molecule translocates more slowly, the relative effect of thermally induced (Brownian) motion on the molecule will increase. The net distance traversed due to Brownian motion scales as the square root of the total time interval. Thus, a molecule that resides at a nominal point for 1 ms will move an average net distance away from that point due to thermal motion that is 32 times further than if it resided for 1 μs. In the case of sequencing DNA, random thermally induced motion sets a limit to how much the measurement time can be practically increased by merely slowing down the translocation rate of the DNA: attempts to measure a single monomer over long time periods allow random thermally induced motion to blur the results by mixing in contributions from neighboring monomers.

Methods developed that attempt to slow down the rate of DNA translocation include the use of hairpins captured in the entry of the channel that stop DNA translocation and unzip slowly, as well as polymerases and exonucleases that act as molecular machines to draw the DNA through the channel base-by-base during the enzyme cycle. In both cases, diffusional motion of DNA is reduced by the tension within the DNA caused by the electric field force pulling against the translocation limiting mechanism. However, the DNA hairpins can only be used as short strands of DNA, and the enzyme methods have not yet advanced to the point that they can control the translocation rate of a molecule.

Recently, variations in the hairpin approach have allowed the detection of distinct, individual blocking signals for all four DNA bases, with signal differences in the order of ~1 picoamp (pA) to 4 pA (at 120 mV bias). In addition, detection of a single base change within a polybase chain has been shown, indicating that only a single base is needed for measurement. Based on these measured signal amplitudes, present ionic current recording technology is in the order of 100 times too insensitive at the detection bandwidths (short measurement durations) that are required.

Accordingly, what is needed is a system and method to reduce the translocation velocity of a molecule through a detection channel and the diffusional motion of the molecule, while translocating, that is not limited to short molecular lengths and, in addition, does not inherently act to reduce the current blocking signal of interest.

SUMMARY OF THE INVENTION

The present invention is directed to an electrolytic sensing system and method for measuring a channel blocking signal and providing controlled translocation of at least one polymer, such as ssDNA, through a fluid channel. In general, the system includes a first fluid chamber containing a first electrolyte, a second fluid chamber containing a second electrolyte, and a barrier separating the first and second fluid chambers, with the barrier having at least one fluid channel therein. The barrier is attached to a temperature control stage, which is adapted to cool the system, thus reduce thermally induced motion of the polymer within the system. Optionally, a membrane with an associated protein pore, such as aHl, may be utilized in conjunction with the fluid channel. The protein pore may be modified to improve the channel blocking signal, improve spatial resolution of the channel blocking signal within the length of the molecule and/or decrease the mobility of the molecule.

In use, a substantially constant electric field supplied by a DC power source is applied across the fluid channel via bias electrodes and induces translocation of the molecule within the system. Additionally, an oscillating electric parameter supplied by an AC power source (e.g. voltage source or current source) is applied across the fluid channel. After a polymer enters the channel, a sensor detects blocking signals produced by the polymer's monomers as they move through the channel. The signals undergo filtering and demodulation before a preliminary estimate is projected of the blocking signal as a function of distance along the polymer. The amplitude of the signal is then compared to calibrated values to project the nature of the monomers present. The substantially constant electric field can be altered to provide more detailed control of the polymer and, optionally, run a polymer through the channel multiple times to provide numerous signal readings. Additionally, a desired combination of AC amplitude and frequency may be selected to oscillate the polymer back and forth within the channel between two monomers, thus allowing the signals from each to be increased by averaging synchronously with the applied field.

Advantageously, the present system significantly reduces the translocation velocity of a polymer through an ion channel, as well as the diffusional motion of the polymer while translocating. Additionally, the system and method allow for long molecular strands to be sequenced quickly without amplification, and without inherently reducing the blocking signal of interest.

Additional objects, features and advantages of the present invention will become more readily apparent from the following detailed description of preferred embodiments when taken in conjunction with the drawings wherein like reference numerals refer to corresponding parts in the several views.

DETAILED DESCRIPTION OF THE PREFERRED EMBODIMENTS

Figure 1A:
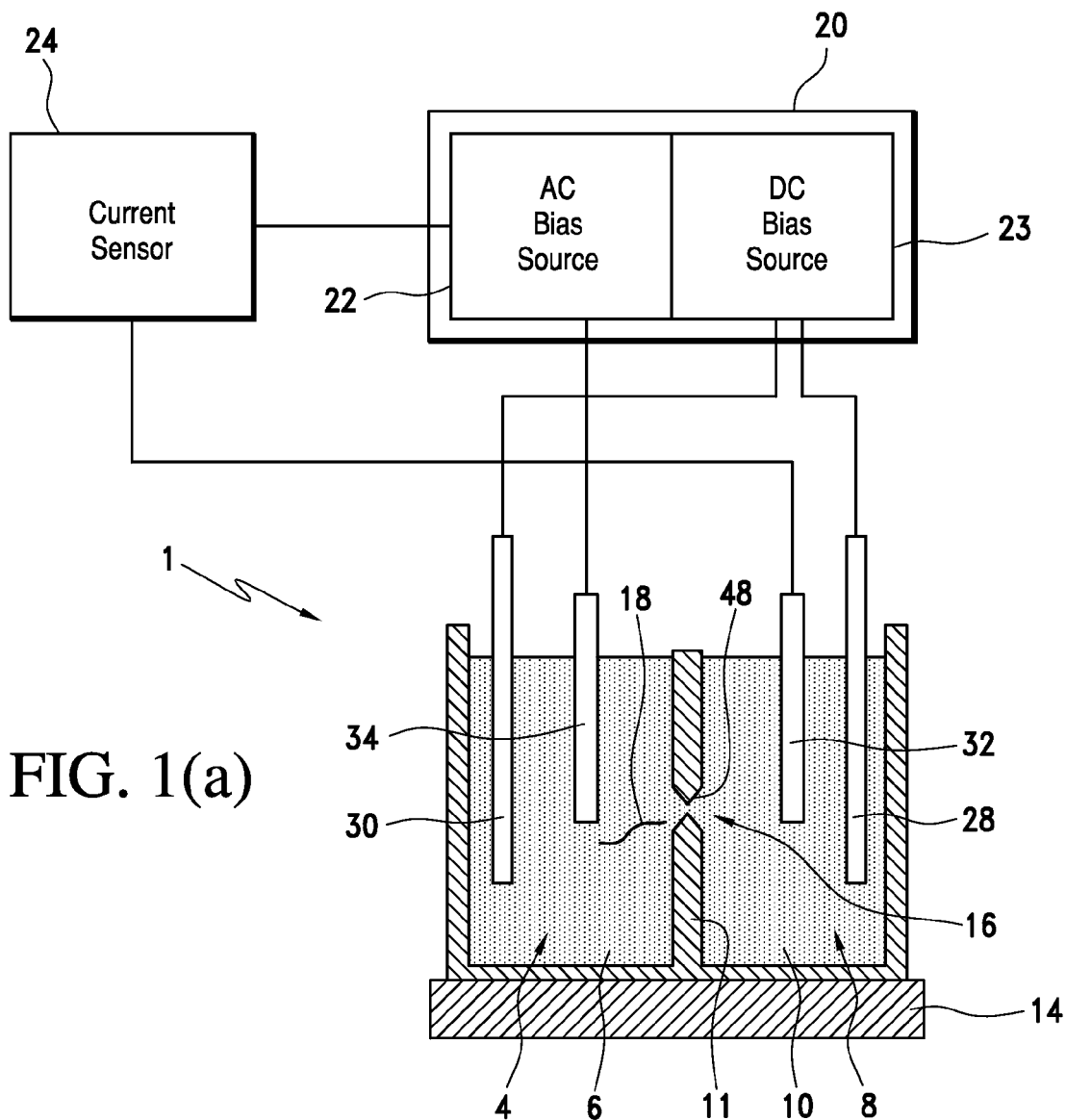
FIG. 1(a) shows a cross-sectional view of an electrolytic sensing system in accordance with the present invention.

In general, the present invention is directed to a method and electrolytic sensing system for controlling the translocation of a molecule or polymer through a channel, in order to measure blocking signals corresponding to individual monomers. With initial reference to FIG. 1(a), sensing system 1 includes a first fluid chamber or electrolyte bath 4 within which is provided a first electrolyte 6, and a second fluid chamber or sensing volume 8 provided with a second electrolyte 10. Sensing volume 8 is separated from electrolyte bath 4 by a barrier structure 11, fluid path connecting first and second electrolytes 6 and 10. In an alternative embodiment depicted in FIG. 1(b), system 1 includes a barrier structure 11' having multiple channels 16' therein to provide for an array-type sensing system. Regardless, barrier structure 11 is joined to a substrate or stage 14. In a preferred embodiment, stage 14 is a temperature control stage. In general, system 1 controls the translocation of a polymer 18 through channel 16 utilizing a translocation means or power source 20. In the embodiment of FIG. 1(a), translocation power source 20 includes an AC bias source 22 and a DC bias source 23. A current sensor 24 is provided to measure the AC current through channel 16 produced by the AC bias source 22. Current signals detected by current sensor 24 are processed in order to calculate the monomer sequence of polymer 18, as will be discussed in more detail below.

Electrolytes 6 and 10 are typically the same and biocompatible (e.g. 1 M KCl). Preferably, electrolytes 6 and 10 have the highest concentration compatible with other aspects of system 1 in order to maximize the current that flows through channel 16 for a given applied voltage. In some applications, electrolytes 6 and 10 are different in order to drive an electrical current through channel 16 via a concentration gradient across the channel. Driving the current in this manner provides a way to induce the desired current for a current blocking signal without applying a direct electric force on polymer 18 via an imposed electric field. A concentration driven current can be used in conjunction with a current produced by applied DC or AC electric fields if desired.

Channel 16 must be small enough that polymer 18 produces a measurable blocking signal when located within the channel. In the case where polymer 18 is DNA, channel 16 preferably has a diameter in the order of 2 nanometers (nm) at its narrowest point. In the embodiment shown in FIG. 1(c), channel 16 is provided with an ion channel or protein pore 38 inserted into a thin membrane 40 that spans the larger, and thus more easily fabricated, channel 16. When system 1 is utilized in the sequencing of single strand DNA (ssDNA), indicated at 18' in FIG. 1(c), channel 16 preferably includes a biological protein pore 38 such as aHl. One advantage of this approach is that such a protein pore 38 can be modified at the molecular level in a manner known in the art in order to modify its interactions with polymers inside the pore. Such modifications may increase the blocking signal, change the spatial distribution of the blocking effect, or decrease the drift and/or diffusional velocity of the molecule being measured.

When utilized, membrane 40 can be a lipid bilayer, an equivalent material such as polydimethylsiloxane (PDMS), a liquid film or even a solid material that allows pore or ion channel insertion in some manner. Membrane 40 is formed over channel 16 by the method of painting, by vesicle fusion or by another method known in the art. One such membrane configuration is described in pending U.S. Provisional Patent Application Ser. No. 60/919,694 to White et al.

Barrier 11 is preferably a nanomachined very low conductivity silicon or an equivalent hard substrate such as glass, plastic (e.g. polyimide), quartz or sapphire. Alternatively, a conventional Teflon cup apparatus or patch clamp pipette may be utilized. The principal requirements for barrier 11 are that it provides an electrical resistance (including the seal resistance to the membrane if one is used) between electrolyte bath 4 and electrolyte 10 in the order of 10 gigaohms (GΩ). For example, lipid membranes on glass produce a seal 10 GΩ or higher. In addition, for operation at higher AC frequencies (>10 kilohertz (kHz)) barrier 11 must be made of a material with low dielectric loss tangent.

Further, in order to measure the rapid changes in signal between individual monomers of a polymer, it is necessary to minimize the capacitance coupling electrolytes 6 and 10. This capacitance is given by the formula $C = \in A/t$, where A and t are the area and thickness respectively of barrier 11. Overall, the capacitance that couples the inner electrolyte volume 8 to the outer electrolyte volume 4 across structure 11 is preferably less than 2 picofarad (pF) and more preferably less than 0.25 pF. Specific configurations of barrier 11 and of channel 16 that achieve the desired low values of coupling capacitance are taught in pending PCT Application No. PCT/US2007/011257 to Hibbs and Poquette, which is hereby incorporated by reference.

In practice, a polymer of interest 18 is introduced into electrolyte bath 4, as depicted in FIG. 1(*a*). Electrodes 28 and 30 are connected to DC bias source 23 and provide an electric field across channel 16 that drives polymer translocation and electrical bias current through the channel. Preferably, electrodes 28 and 30 produce a DC field across channel 16. When utilizing a DC field, electrodes 28 and 30 are made of a material that couples to electrolyte 6 and 10 via exchange of electrons and accordingly have a real component to their impedance. Preferably, electrodes 28 and 30 are made of a conventional non-polarizable material, such as silver/silver chloride (Ag/AgCl). FIG. 1(*a*) shows additional electrodes 32 and 34 immersed in the fluid wherein electrode 32 is connected to current sensor 24 and electrode 34 is connected to AC bias source 22. If desired, the same electrodes could be used for bias and readout. If separate DC bias and AC bias electrodes are used, electrodes 32 and 34 are preferably made from a material, such as platinum, that couples to the electrolyte in a predominantly capacitive manner.

Polymer 18 is drawn from the bulk solution or electrolyte 6 towards channel 16 by electrophoresis, essentially increasing its concentration in the region of channel 16. In order to experience a force from applied DC and AC electric fields, polymer 18 preferably has a net electric charge, which can be inherent to its solvated state or induced or modified by adjusting the solution conditions (e.g. The pH of electrolyte 6, 10). Even though the water surrounding polymer 18 in solution produces some shielding of this charge, there is still a net charge that allows for polymer 18 to be driven through channel 16 via an applied electric field. A reduced polymer charge can be compensated for by increasing the applied electric fields. In some cases, a polymer of interest may be insufficiently charged to be pulled into channel 16 without applying a voltage that damages system 1 (e.g. ruptures a lipid bilayer). However, in general, a low polymer charge is beneficial because it limits polymer velocity in response to the field, which in turn allows a higher bias field to be used, and thereby a higher bias current. Thus, the chemical environment in electrolyte 6 and 10 (e.g. pH, electrolyte concentration) is preferably set so as to minimize the polymer charge.

Once at the mouth of channel 16, there is, in general, an energy barrier to get polymer 18 to enter a narrow measurement region 48 and/or a pore of channel 16. For example, for ssDNA 18' entering an aHl protein pore 38, a DC voltage in the order of 70 millivolts (mV) must be applied in order to initiate entry. This can be overcome by holding the DC voltage at a high enough level to induce insertion, and then quickly reducing the DC voltage as soon as the polymer insertion has occurred in order to reduce the polymer translocation rate to a desired lower level. If desired, the applied DC voltage can be set to zero for periods of measurements, with short periods of small voltage to induce motion. This requires detecting the initial insertion signal within the order of 1-10 microseconds (μs) and reducing the applied DC voltage over a period of time in the order of 1-10 μs. The change in current produced by a polymer 18 entering an appropriate pore 38 is large (e.g. up to 80% of the total current for ssDNA in aHl, corresponding to ~80 picoamps (pA) at a voltage of 100 mV). Therefore, it is relatively easy to detect the insertion of a polymer 18 within a short period of time.

Figure 2:
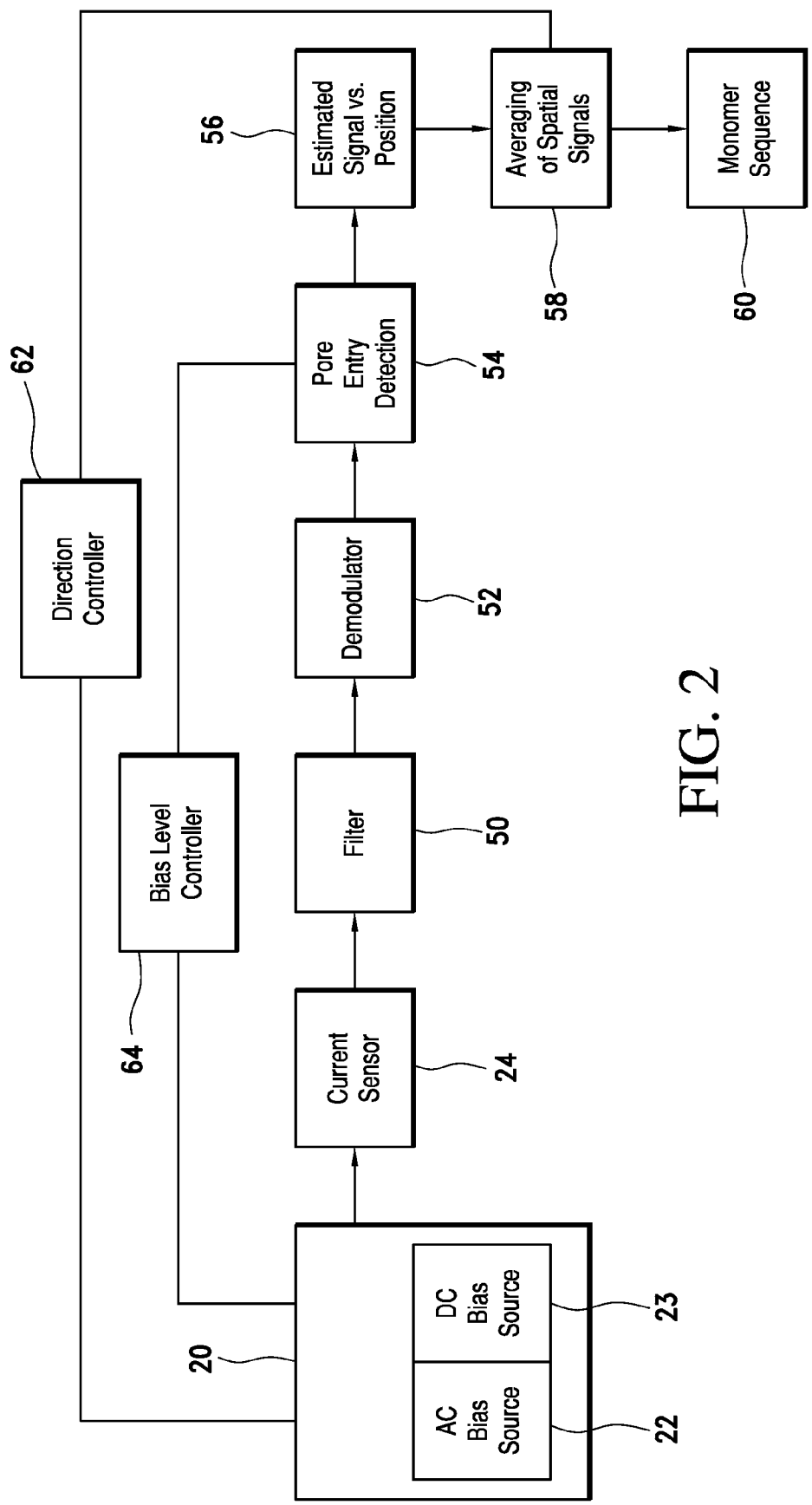
FIG. 2 is a flowchart depicting the processing of a current blocking signal.

The general manner in which system 1 is utilized will now be discussed with reference to FIG. 2. AC current that flows in response to the applied AC electric field is used to probe the conductance of measurement region 48 as it is blocked by polymer 18. System architectures particularly suitable for measuring the AC current are described in previously cited PCT Application No. PCT/US2007/011257 to Hibbs and Poquette. Preferably, current sensor 24 is as close as possible to sensing electrodes 32 and 34, and all other precautions are taken to minimize stray impedance. In order to maximize the measurement signal to noise ratio (SNR), the bias current signal from current sensor 24 is sent to a narrow band filter 50, where it is filtered about the applied AC frequency, and next demodulated at a demodulator 52 to recover its time domain variation by analog or digital methods known to those familiar with the art. The demodulated signal is then sent to a detection module 54 where an algorithm may be utilized to determine that polymer 18 is ready to be measured. The conductance of the blocked channel can then be compared to calibrated values to project the nature of the molecular unit present in channel 16, as indicated at 56. Calibrated values may be derived from previously measured signals as known simple polymer sequences translocate through channel 16. In some cases, an adequate estimate of the molecular structure can immediately be inferred. However, in others, it will be beneficial to reverse the direction of translocation and record the signal multiple times in order to average many readings as indicated at 58, and thereby improve measurement fidelity, as will be discussed in further detail below. In addition, although measurement parameters should be chosen to reduce the likelihood that the position of a monomer within a strand would become uncertain due to diffusional effects, repeated measurements provide a means of detecting and correcting such errors. The direction of translocation can easily be reversed by reversing the sign of the applied DC bias field utilizing a controller 62. Such gathering of redundant data can be performed on whatever distance scales are desired. The length of the polymer moved in each direction might be as small as a single base, or could be as long as the entire strand. The later option merely utilizes a detection algorithm, similar to that which detected the entry of polymer 18 in channel 16. Such an algorithm detects the onset of the exit of polymer 18 from channel 16, and reverses the DC bias field before it has fully exited. As indicated at 64, a bias level controller is utilized to further control translocation of polymer 18.

Figure 3:
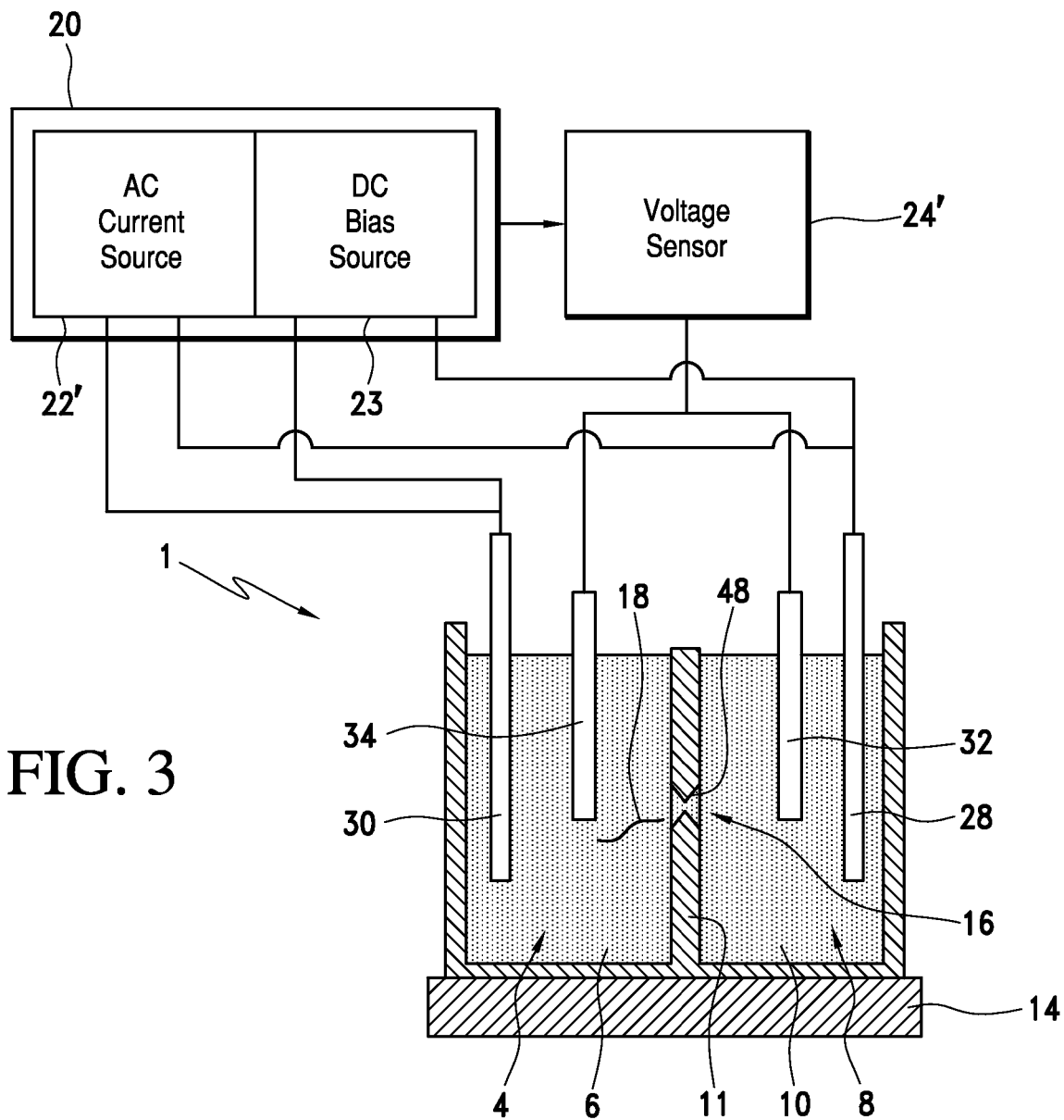
FIG. 3 shows an alternative to the system in FIG. 1(a), wherein an AC current bias and AC voltage sensor are utilized.

The specific hardware and process described above utilize an applied AC voltage bias and an AC current measurement to infer the conductance of the channel as it is blocked by the molecule. The conductance can be correspondingly measured by applying an intentional AC current and measuring the resulting AC voltage. This arrangement is shown in the embodiment of FIG. 3 which a voltage sensor 24' is coupled to electrodes 32 and 34 and senses the voltage in the vicinity of channel 16. Because of the narrow constriction of channel 16, the voltage measured in the bulk fluid region on either side of channel 16 will be substantially the voltage across the channel. As in the case of fixed AC voltage, the electrodes 32 and 34 can be either AC or DC coupled to the electrolytes 10 and 6. The AC and DC signals can be applied through the same pair of electrodes 28 and 30 as shown in FIG. 3, or an additional pair of electrodes (not shown) can be used to allow separate application of AC and DC fields in order to optimize the electrode properties for each. In either case, the DC bias source must present a high impedance at the AC frequency.

When using the alternate arrangement of FIG. 3, the general manner in which system 1 is utilized as discussed earlier with reference to FIG. 2 needs to be slightly modified. In this alternative arrangement, the AC voltage that is generated in response to the applied AC electric as field is used to probe the conductance of measurement region 48 as it is blocked by polymer 18. More specifically, in the first arrangement of FIG. 1(a), the element which applies an oscillating electrical parameter is the AC voltage source 22, while the element utilized in the arrangement of FIG. 3 is an AC current source 22'. Furthermore, in the first arrangement, current sensor 24 is utilized while, in the second arrangement, voltage sensor 24' is utilized. The rest of the process remains unchanged. In a similar manner, a person skilled in the art will be readily able to convert references to voltages and currents appropriately to apply application concepts to either arrangement. Therefore, the discussions that follow regarding details of system optimization is written only in terms of the first arrangement utilizing an AC voltage bias and AC current measurement.

Methods by which system 1 is preferably optimized will now be discussed in more detail. No matter how small its charge, polymer 18 moves back and forth in response to the applied AC field. The amplitude, $V_{ac}$, and frequency, $f_{ac}$, of the AC bias voltage must be carefully set to prevent a polymer 18 moving too far under the influence of the applied AC electric field within the time window of an individual measurement. The total distance moved, $x_{ac}$, depends on the amplitude of the AC potential, $V_{ac}$, and the time it is applied with one polarity, $\frac{1}{2} T_{ac}$, (i.e. half the period of its oscillation). For a given desired $x_{ac}$, the ratio of the AC bias amplitude, $V_{ac}$, and the AC frequency, $f_{ac}$ ($f_{ac}=1/T_{ac}$), is preferably kept constant. If the AC amplitude is too high, polymer translocation will be dominated by the AC bias and the signal of multiple monomers or bases averaged. Motion due to the AC bias can be minimized by increasing the AC frequency so that the total distance polymer 18 moves during the AC cycle is reduced. In general, it is desirable to maximize $V_{ac}$ in order to maximize the amplitude of the blocking current signal.

In a first embodiment A, $V_{ac}$ and $T_{ac}$ are set so that $x_{ac}$ is less than approximately one half of the average distance, $x_{sp}$, between the monomers of a polymer 18 so that the signal from adjacent monomers does not become averaged together. The particular maximum $x_{ac}$ that can be used depends on the specific variation of the net polymer blocking signal with the internal monomer ordering. For example, the average translocation rate at 20° C. for ssDNA is about 2 µs per base for $V_{ac}$=100 mV. Using $T_{ac}$ ~2 µs for the AC bias will prevent ssDNA translocating to the next base before the AC electric field is reversed. Thus, for ssDNA at room temperature, the ratio $V_{ac}/f_{ac}$ is on the order 0.2 V/MHz. In embodiment A, the signal measurement frequency, $f_{meas}$, is set to $f_{ac}/p$, so that the blocking signal associated with a portion of the ssDNA is measured once per p oscillations of polymer 18.

Although desirable, it is not necessary that the AC measurement bias be fast enough and low enough amplitude that polymer 18 moves by less than one monomer per AC cycle. If polymer 18 moves back and forth a statistically predictable amount, signal processing techniques can be used to appropriately ascribe the measured values to expected locations along polymer 18. For example, one method of improving measurement fidelity is to move polymer 18 back and forth between adjacent units (e.g. monomers) under the direct influence of the AC field. By using an appropriate combination of AC amplitude and frequency, polymer 18 can be oscillated back and forth between two monomers to allow the signal from each to be increased by averaging synchronously with the applied field. A further benefit of this approach is that a higher amplitude AC current can be induced, thereby increasing the signal to noise ratio of the measurement. Once sufficient signal has been acquired, polymer 18 can be translocated by the desired amount to read the next monomer, allowing the sequence to be built up from the overlapping signals.

Figure 4:
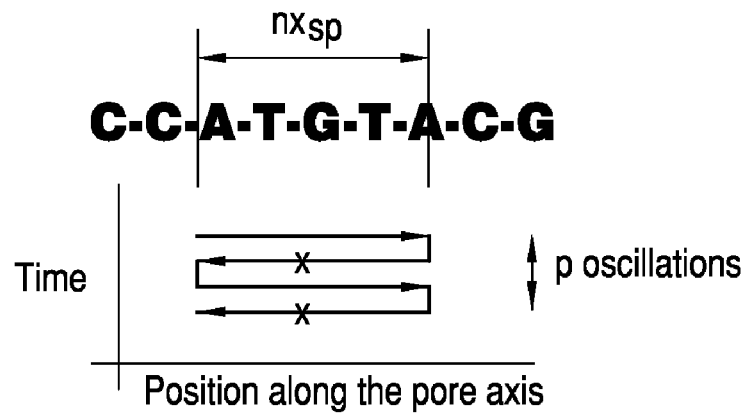
FIG. 4 depicts the position of a single strand DNA over time as it is driven back and forth through a pore.

In a second embodiment B, the requirements on $V_{ac}$ and $T_{ac}$ are relaxed such that $x_{ac}$ can be of the same order or larger than $x_{sp}$. $V_{ac}$ is set so that $x_{ac}$ corresponds to a number, n, of monomer spacings. Although it is not essential that n be an integer, it is conceptually, and possibly mathematically, easier for it to span an even number of monomers, and therefore approximately integral, preferably differing from integral by less than 25%. In embodiment B, polymer 18 is driven back and forth through channel 16 by n monomers. This methodology is depicted schematically in FIG. 4 using ssDNA as the polymer of interest and a protein pore having an AC amplitude of $nx_{sp}$(n~5). The data samples are shown as crosses in FIG. 4, and each data point is the average of the blocking signal over the length $nx_{sp}$ of the polymer. The signal sampling frequency, $f_{meas}$, rate is set to $f_{ac}/p$, and the blocking signal associated with the length $nx_{sp}$ of polymer 18 is measured once per p cycles. The net signal at each data point is an appropriately weighted average of the portion of the polymer strand oscillating back and forth over multiple monomers, rather than a single monomer location. The means to deconvolve this blurring out of the signal will be discussed below as part of the larger question of the method to resolve a delocalized signal. The AC oscillation can be repeated as many as p times if desired. The benefit of embodiment B is that a larger $V_{ac}$ can be used, thereby increasing the current passing through channel 16, and thereby increasing the blocking signal associated with each monomer of polymer 18.

Once the polymer 18 has been pulled through channel 16 once, the direction of the DC bias potential, $V_{dc}$, can be reversed and the entire strand pulled through in the opposite direction. The point of reversal can be determined by setting an appropriate threshold in the bulk blocking signal of polymer 18 in the same manner as used to initiate polymer entry. On each pass of polymer 18 through channel 16, the time record of the base by base blocking signal is reversed and added to the total accumulated record. This process can be repeated as many times as necessary to reach the required measurement accuracy. To minimize the effect of diffusion, when comparing these multiple signals from the same polymer, regions in the signal that contain signal features of large magnitude relative to the noise can be used for alignment between the signals. For instance, in the case of DNA, the consideration of repeated signals may be required to definitively observe the difference between a cytosine (C) and guanine (G) base, but transitions between cytosine (C) and thymine (T), which produce a much larger signal, will be clearer in each individual signal.

An additional method to control polymer translocation that is independent of the means used to readout the pore blocking current signal is to induce a fluid flow within channel 16 countering the molecular velocity. Such a flow also produces a fluid boundary layer that can act to reduce the lateral motion of polymer 18 within channel 16. Likewise, the presence of a pressure gradient and/or flow may slightly alter a pore's structure or polymer/pore interactions to slow polymer drift or diffusion.

Figure 5:
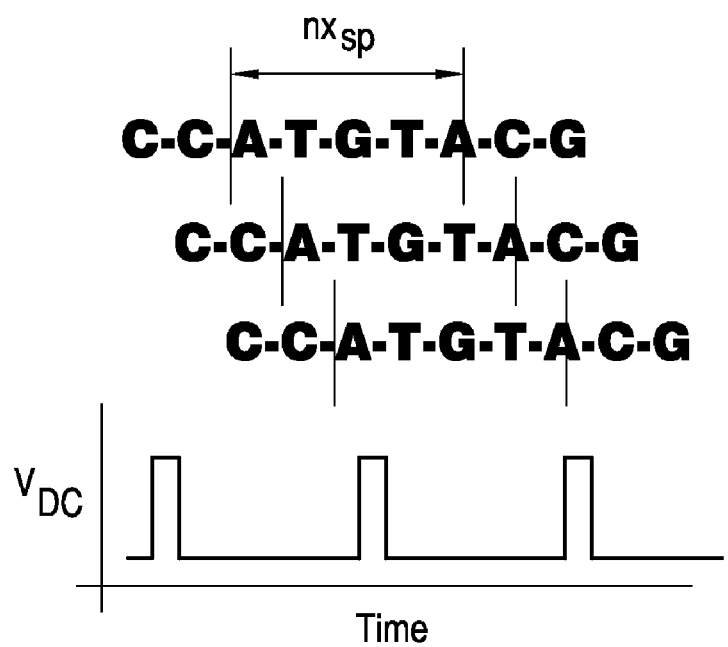
FIG. 5 depicts changes in DC bias potential as a single strand DNA is driven back and forth through a pore over time.

According to the invention, the means to effect the bulk translocation of polymer 18, the DC field, is controlled separately from the means used to identify the monomer (the AC field). In both embodiments A and B, the DC bias potential, $V_{dc}$, must be set sufficiently low that it does not significantly perturb the position of the monomer on the timescale of the measurement. Thus, the distance polymer 18 moves in response to the DC field, $x_{dc}$, during the total time of the measurement, $pT_{ac}$, associated with a given monomer or set of monomers, should be small compared to $x_{sp}$, i.e. $x_{dc} < \frac{1}{2} x_{sp}$. Preferably, the DC field is set to zero during measurement interval $pT_{ac}$, and then applied for a short duration to advance polymer 18 through channel 16 by the required linear increment, i.e. $nx_{sp}$. The maximum value of $V_{dc}$ is the breakdown voltage of barrier 11 and channel 16. To increase measurement accuracy, and to minimize the risk of a region of polymer 18 being skipped, the length $nx_{sp}$ of polymer 18 that is probed can be overlapped as shown in FIG. 5.

The discussion to this point implicitly assumes that channel 16 has an internal constriction or measurement region 48 such that the blocking signal is predominantly produced in a region that is small compared with the spacing between the monomers. In this case, the change in channel current blocking signal can be predominantly attributed to the monomer that is within measurement region 48, and that signal will have an abrupt transition between values as one monomer exits measurement region 48 and the other moves in. Indeed, in this ideal case, there may be signal structure on a scale smaller than a monomer. However, in many cases measurement region 48 will be at least the same size as a monomer or larger, resulting in a smoothly varying signal between bases. In addition, even though the portion of polymer 18 in the narrowest part of channel 16 may affect the measured signal most strongly, blockages in less-constricted portions may produce a measurable effect. A measured signal at any particular time can be considered a convolution between all the monomers in any portion of channel 16 with a convolution function that depends on the geometry and/or chemical properties of each position within channel 16. The magnitude of the convolution function may be greatest at measurement region 48 of channel 16, but will likely be non-zero along the entire length of the channel.

Ideally, the structure of channel 16 is chosen such that the shape of the relative blockage signal produced by a given monomer as a function of position through the channel is the same for each kind of monomer, with merely the magnitude being different. This structure allows the resulting deconvolution problem to be solved mathematically with methods known to those skilled in the art. If this is not the case, either a suitable homomorphic transformation can be used, or an iterative method can be used, one example of which is discussed below. Further, the blurring due to subsampling discussed in embodiment B above will produce an additional convolution with a kernel of width $x_{ac}$. If this is mathematically well behaved, it may be deconvolved analytically before iterative methods are applied for the pore-length-effect deconvolution.

The specific form of the channel-related convolution function depends on the specific polymer and channel combination. However, the function can be directly probed, and therefore used in subsequent signal processing stages by empirical measurements of known polymer sequences. For instance, the signal can be measured from a ssDNA segment comprised of a long length of identical bases (e.g. adenine (A) bases) with a single differing base (e.g. cytosine (C)) in the middle. The length must be long enough to ensure that, once the strand has fully entered channel 16, the signal measured will be for all A bases. As the strand moves through channel 16, the single C base will produce a differing signal characteristic of having the C at each specific position along the length of the channel. Such a measurement can be repeated many times to allow this signal to be determined very accurately. Similar measurements can be done for the other possible combinations of repeated bases (eleven others in the case of DNA's four unique bases) with single differing bases in the middle. In the case that $x_{ac} > x_{sp}$ (embodiment B) the measurement results will be specific to the particular value of the $x_{ac}$ used, unless the $x_{ac}$ blurring is removed separately.

Together, these empirical data sets will allow the blockage signal characteristic of each possible base at every position within channel 16 to be known. Once such convolution functions are known, then any given measured signal can be deconvolved. If the shape of the convolution functions for each base differ only by a constant proportionality factor, then standard mathematical methods can be used. Otherwise, one of many iterative methods can be applied. For example, if channel 16 has a dominant most-constricted point (a location of pronounced highest magnitude in the convolution kernel) then one method includes: a) an initial guess at the actual sequence can be made assuming that the entire observed signal is due to only the base that is present at the most constricted point, b) once a preliminary estimate exists for the sequence, then for each position of the strand, the measured signal can be adjusted to remove the contributions of bases not in the most constricted point, leaving an adjusted signal for the most constricted point, c) on the basis of the adjusted signal, an improved estimate can be made for the base at that constricted position, d) this process can be iterated until there is no further improvement in the match between the measured signal and the signal that is expected for the presumed sequence and the convolution functions. If no dominant most-constricted position exists in the convolution kernel, then more complex iterative methods can be employed which will similarly, iteratively modify an assumed sequence until an optimum match with the measured signal is obtained.

Ideally, the monomer signals are averaged many times ($p \gg 1$) in order to maximize SNR. However, the total measurement time associated with a given monomer or set of monomers ($pT_{ac}$) is limited by molecular motion due to thermal diffusion. For ssDNA, the diffusion constants at 15° C. In the directions of entering a pore with the 3' vs. the 5' end, have been determined to be 3.05 and $1.77 \times 10^{-10}$ $cm^2/s$, respectively. For a diffusion constant, D, of $1.77 \times 10^{-10}$ $cm^2/s$ and t=1 μs, the 1-dimensional diffusion distance $(2Dt)^{1/2}$ is order 0.19 nm, or about 0.45 bases. The effect of diffusion over longer times can be estimated by an analytic solution depending on the geometry; for instance, for one 1-dimensional diffusion with an absorbing boundary at one side (corresponding to polymer 18 exiting channel 16). In Equation 1, $P_{escape}(t)$ is the probability that the strand has escaped channel 16 by time t, d being the number of monomers, D the diffusion constant, and v the velocity due to the DC bias.

$$P_{escape}(t) = \frac{1}{2}\left(\text{erfc}\left(\frac{d-vt}{\sqrt{4Dt}}\right) + \exp\left(\frac{dv}{D}\right)\text{erfc}\left(\frac{d+vt}{\sqrt{4Dt}}\right)\right) \quad \text{Eq 1}$$

Figure 6:
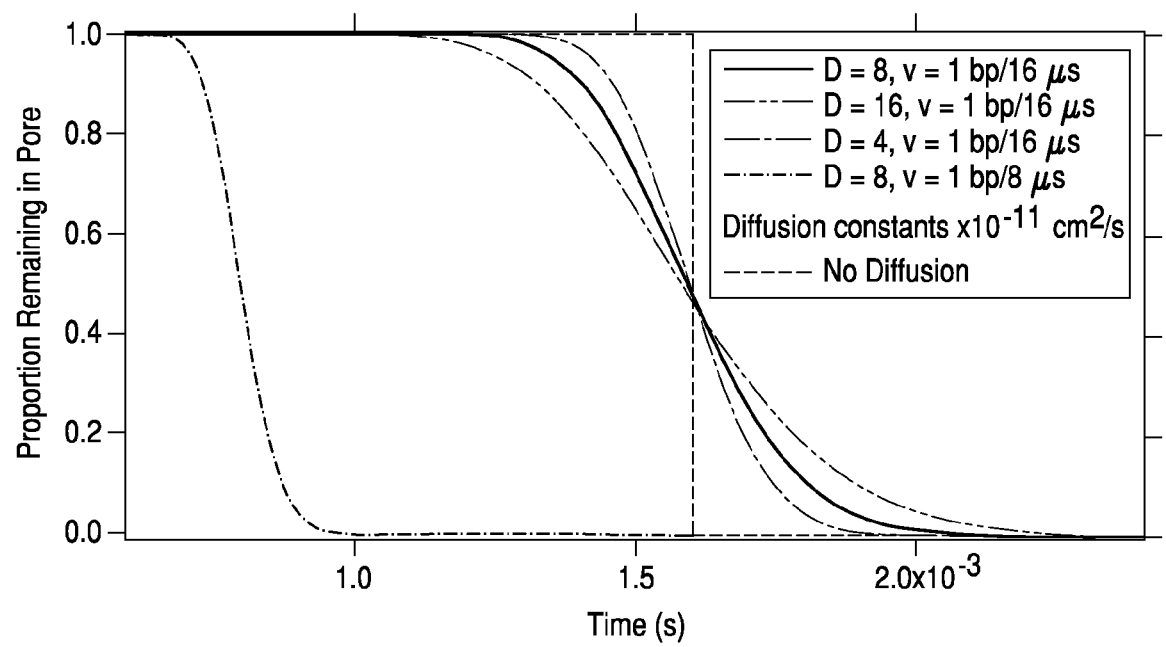
FIG. 6 is a graph of the effect of diffusion on polymer translocation over time.

FIG. 6 shows the effect of different polymer translocation velocities, v (as produced by the DC bias) at fixed D, and different D at fixed v, for a 100-mer strand. The y-axis of FIG. 6 is the proportion of DNA strands remaining in channel 16 at time t. As the diffusion constant increases, the probability distribution broadens over time. A D value of $8\times10^{-11}$ cm$^2$/s and v=1 base/16 µs corresponds to the example embodiment for ssDNA given below.

The AC measurement parameters, $V_{ac}$, $T_{ac}$ and p must be set so that the net motion of polymer 18 due to diffusion, $x_{diff}$, is less than approximately one-half of the average distance, $x_{sp}$, between the monomers in order that the order of the monomer within the chain is not lost. Thus, for ssDNA at 20° C. a total measurement time per monomer in the order of 1 µs is the longest that can be used before thermal motion causes the signal of one monomer to be averaged with its neighbors. As discussed, for most polymers, a measurement time of 1 µs is too short to achieve an adequate recording sensitivity. Therefore, in a preferred embodiment, temperature control stage 14 is utilized to cool electrolytes 6, 10 and thus reduce thermally induced motion. In the case of DNA, measurement of translocation velocity suggest that the diffusion constants change by a factor of 4 on cooling electrolytes 6, 10 from 15° C. to 2° C. This allows the residence time per monomer to be increased by a factor of 4, allowing a nominal 2 times improvement in sensitivity.

The optimum values of $V_{ac}$, $T_{ac}$, $V_{dc}$, T and p depend on the specific polymer to be measured and the properties of the channel and/or pore used. As previously mentioned, DNA is one polymer of significant technical and commercial importance. Accordingly, as an example of a preferred embodiment of the invention, the specific example of sequencing DNA is discussed.

Figure 1B:
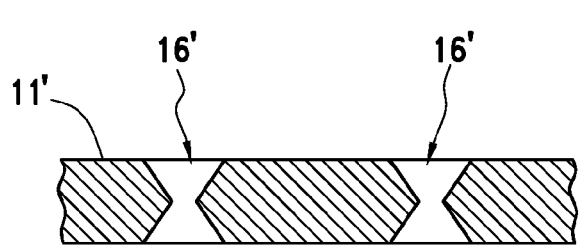
FIG. 1(b) shows a partial cross-section view of a portion of the electrolytic sensing system of FIG. 1(a) including multiple parallel channels.
Figure 1C:
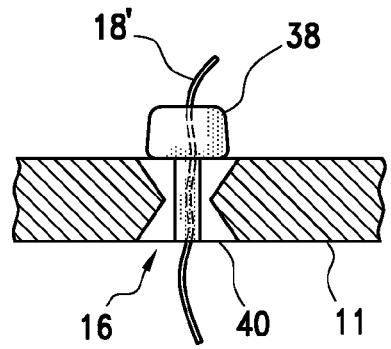
FIG. 1(c) shows a partial cross-section view of a portion of the electrolytic sensing system of FIG. 1(a) including a membrane and protein pore.

Preferably, system 1 is implemented via a method that has improved sensitivity such as the one taught by Hibbs and Poquette, 2007, previously incorporated by reference. In this approach, an aHl protein pore 38 is located within lipid bilayer 40 that spans channel 16 in barrier 11, as depicted in FIG. 1(c). Channel 16 is of nanoscale dimensions, which provides improved mechanical robustness and, importantly, enables the use of higher AC and DC applied voltages.

As outlined above, a $V_{dc}$ is initially set to at least 70 mV in order for ssDNA 18' to enter the aHl protein pore 38. Preferably $V_{dc}$ is set to 200 mV, and most preferably to the breakdown voltage limit of membrane technology, which is presently approximately 750 mV, in order to draw ssDNA 18' to pore 38' by electrophoresis. Once ssDNA 18' entry into measurement region 48 is detected, the $V_{dc}$ is reduced in order to slow down the translocation rate to the desired level as discussed below.

In one preferred embodiment, each electrolyte 6, 10 is 3M KCl and the system is cooled to 2° C. Cooling the system preferably reduces the 1-dimensional diffusion constant to an average value for its two possible directions of travel of approximately $0.5\times10^{-10}$ cm$^2$/s. Most preferably, the system may be cooled to nearly the freezing point of the 3 M KCl. The characteristic diffusion time $T_{diff}$ is the time such that the standard deviation in the position is equal to $x_{sp}$, for 1-dimensional diffusion:

$$T_{diff} = \frac{x_{sp}^2}{2D}.$$

The measurement frequency must be set so that the time between individual measurements, $T_{meas}$ (=p$T_{ac}$) is shorter then the diffusion time ($T_{meas}<T_{diff}$). As a baseline design, we set $T_{meas}=T_{diff}/4$. For ssDNA within an aHl protein pore, $x_{sp}=4\times10^{-8}$ cm giving $T_{meas}=4$ µs, or equivalently $f_{meas}$ (=1/$T_{meas}$)=250 kHz. The frequency of the applied AC bias must be at least $f_{meas}$ and preferably $f_{ac}=2.5$ and $f_{meas}=625$ kHz (i.e. p=2.5).

At 2° C., the average translocation rate for ssDNA through aHl extrapolates to be 16 µs per base for $V_{ac}=100$ mV, which translates to a drift velocity of 0.625 bases/µs at 1 V for a linear dependence of velocity on voltage. Presuming that motion is in phase, the translation for a sinusoidal AC voltage is $X_{ac}$=velocity*$T_{ac}$/2*pi. For $f_{meas}=625$ kHz and $V_{ac}=1$V, Tac=1.6 µs and $x_{ac}=0.16$ bases. Setting $V_{ac}$ to 1 V compared to the conventional DC bias voltage level of 125 mV has the benefit of increasing the average AC current blocking signal by a factor of 8(=1/0.125). Operating in 3M KCl increases the blocking current by a further factor of nearly 3. Measurements using trapped DNA suggests a lower limit of 1 pA (for $V_{dc}=125$ mV) difference in current blocking signal between DNA bases. Thus, the projected minimum blocking signal difference between DNA bases using an AC readout approach according to the preferred embodiment is approximately 24 pA (1*8*3).

Figure 7:
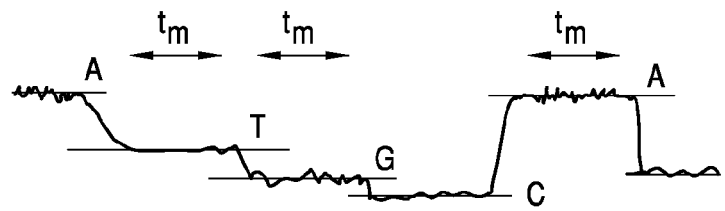
FIG. 7 depicts the idealized measurement of DNA bases over time utilizing the electrolytic sensing system of the present invention.

An idealized base-by-base measurement of DNA is shown in FIG. 7. For visual convenience, each base is portrayed (i.e. adenine (A), thymine (T), guanine (G), cytosine (C)), producing a roughly constant current blocking signal for an approximately regular time $t_m$, while in measurement region 48 with an abrupt change in amplitude between bases. However, it is not necessary that the signal change between bases be abrupt, only that: a) an adequate measurement SNR is achieved for each base, and b) the DNA moves in a sufficiently monotonic manner that the order of the bases is generally preserved.

Setting $f_{meas}=250$ kHz produces an effective noise bandwidth of 125 kHz. For a system of the type taught by Hibbs and Poquette, 2007, previously incorporated by reference herein, at a bandwidth of 125 kHz, the equivalent current noise is approximately 5 pA$_{rms}$. Thus, the SNR for each measurement point in the preferred embodiment is nearly 5. The SNR can be further increased by making multiple measurements of each base. If $V_{dc}$ is set to 200 mV, a given base will be recorded for 8 µs. Alternatively, $V_{dc}$ can be set to zero for 8 µs (or another desired time interval) and then set to 1 V for 1.6 µs to advance the ssDNA by one base. As noted above, in this preferred embodiment for ssDNA, $T_{diff}=16$ µs. Thus, two measurement points per base can, in general, be acquired, increasing the SNR by a factor of 1.4. A further improvement can be achieved by reversing the polarity of $V_{dc}$ one or more times and adding the signal coherently over the entire length of the strand or over regions defined by the larger changes in blocking current between bases.

The overall measurement throughput of system 1 may be limited by both the time taken to draw polymer 18 into channel 16 and the time required to measure polymer 18 within channel 16. Throughput can be improved by using multiple measurement channels in parallel, as depicted in FIG. 1(b). Depending on the physical design of channels 16', they may all be formed in the same substrate, or may be in separate substrates. Likewise, they may share one or both of the electrolyte volumes and measurement electrodes. Indeed, if the arrival statistics dominate the measurement time, then it is unlikely that more than one of multiple parallel channels 16' would contain a molecule and the pores can share both electrolyte volumes and measurement electronics, merely at the cost of additional current noise being drawn through the unoccupied pores. This can be eliminated by sharing only one electrolyte volume and one electrode in an array configuration similar to that taught by International Publication No. WO 2006/044248, hereby incorporated by reference.

Another important benefit is the speed of detection. At 16 μs/base, system 1 can read on the order of 50,000 bases/sec. The system can easily be scaled to have 50 parallel channels. In theory, this would allow a 3 billion base mammalian genome to be sequenced in under an hour, a 1000 times improvement over present systems. Such rapid low cost sequencing could be used to obtain individualized information on predisposition to diseases and treatments and could thereby revolutionize medicine.

The electrolytic sensing system 1 of the present invention allows for direct electronic readout of molecular structure, which offers a near ideal approach to DNA sequencing with numerous benefits over prior sequencing technologies. For example, the system of the present invention: 1) operates on a single molecule without need for an amplification step, removing the associated multi-hour processing step, amplification equipment, and the associated possibility of error; 2) requires essentially no consumables; 3) allows for easier determination of repeat segments of DNA since the measurement can be made on a single copy; 4) allows for repeat measurements and storage because the sample is not destroyed; 5) has the potential to read 10,000 or more base lengths, thus significantly simplifying the post processing needed to reassemble a long sequence; 6) may have a low system size, weight, and cost, as well as portability; and 7) offers rapid sequencing of RNA, because it does not require reverse transcriptase to recreate DNA fragments. This could eventually enable rapid in situ sequencing of viral RNA for applications such as detection of avian flu.

Although described with reference to preferred embodiments of the invention, it should be readily understood that various changes and/or modifications can be made to the invention without departing from the spirit thereof. For instance, while described with reference to ssDNA, it should be understood that the system of the present invention can be utilized to measure the physical configuration of any suitable molecule. In general, the invention is only intended to be limited by the scope of the following claims.

We claim:

1. An electrolytic sensing system for measuring the current blocking signal of a molecule comprising:
    a first fluid chamber containing a first electrolyte;
    a second fluid chamber containing a second electrolyte;
    a barrier separating the first and second fluid chambers and having a first channel therein defining a measurement region and providing fluid communication between the first and second fluid chambers;
    a DC source adapted to apply a substantially constant electric field across the measurement region via electrodes in electrical contact with respective first and second fluid chambers to induce translocation of a molecule through the measurement region in a controlled manner;
    an AC source adapted to apply an oscillating electrical parameter across the measurement region via an electrode in electrical contact with one of the respective first and second fluid chambers, the oscillating electrical parameter having a frequency; and
    a sensor adapted to detect a channel blocking signal associated with the oscillating electrical parameter.

2. The electrolytic sensing system of claim 1, wherein the oscillating electrical parameter is an AC voltage and the sensor is a current sensor.

3. The electrolytic sensing system of claim 1, wherein the oscillating electrical parameter is an AC current and the sensor is a voltage sensor.

4. The electrolytic sensing system of claim 1, further comprising an electrolyte temperature control stage.

5. The electrolytic sensing system of claim 1, wherein the frequency of the oscillating electrical parameter is greater than 20 kHz.

6. The electrolytic sensing system of claim 5, wherein the frequency of the oscillating electrical parameter is greater than 100 kHz.

7. The electrolytic sensing system of claim 1, further comprising a protein pore located within the first channel.

8. The electrolytic sensing system of claim 7, further comprising a membrane spanning the first channel.

9. The electrolytic sensing system of claim 8, wherein the membrane is selected from the group consisting of a lipid bilayer, polydimethylsiloxane (PDMS), and a liquid, film.

10. The electrolytic sensing system of claim 8, wherein the protein pore is located within the membrane.

11. The electrolytic sensing system of claim 7, wherein the protein pore is alpha-hemolysin.

12. The electrolytic sensing system of claim 7, wherein the protein pore is a modified protein pore adapted to improve the blocking signal.

13. The electrolytic sensing system of claim 7, wherein the protein pore is a modified protein pore adapted to improve spatial resolution of the blocking signal within the length of the molecule.

14. The electrolytic sensing system of claim 7, wherein the protein pore is a modified protein pore adapted to decrease the mobility of the molecule.

15. The electrolytic sensing system of claim 1, wherein the barrier is selected from the group consisting of glass, sapphire, quartz, high resistivity silicon and plastic.

16. The electrolytic sensing system of claim 1, further comprising a second channel provided in the barrier in parallel with the first channel.

17. The electrolytic sensing system of claim 16, wherein the first and second channels are discrete channels that extend through said barrier.

18. The electrolytic sensing system of claim 1, wherein the first and second electrolytes have a maximum concentration adapted to increase amplitude of the blocking.

19. The electrolytic sensing system of claim 1, wherein the first and second electrolytes are adapted to minimize the charge on the molecule.

20. The electrolytic sensing system of claim 1, wherein the first and second electrolytes are different in order to drive an electrical current through the first channel via a concentration gradient across the first channel.

21. A method of sequencing a polymer in an electrolytic sensing system comprising a first fluid chamber containing a first electrolyte; a second fluid chamber containing a second electrolyte; a barrier having a channel therein and defining a narrow measurement region, said barrier separating the first and second fluid chambers; a DC source adapted to apply a substantially constant electric field across the measurement region via electrodes in electrical contact with respective first and second fluid chambers; an AC source adapted to apply an oscillating electrical parameter across the measurement region via an electrode in electrical contact with one of the respective first and second fluid chambers; and a sensor, the method comprising:
- introducing a polymer to the first fluid chamber;
- applying a substantially constant electric field across the channel utilizing said DC source to provide a translocation force to the polymer;
- applying an oscillating electrical parameter across the channel utilizing said AC source;
- measuring the oscillating electrical parameter to detect a blocking signal when the polymer is within the channel; and
- filtering and demodulating the blocking signal to generate a measured signal indicative of a particular monomer or set of monomers of the polymer.

22. The method of claim 21, wherein the AC source is an AC voltage source and the oscillating electrical parameter is an AC current.

23. The method of claim 21, wherein the AC source is an AC current source and the oscillating electrical parameter is an AC voltage.

24. The method of claim 21, wherein the oscillating electrical parameter is sinusoidal with a frequency greater than 20 kHz.

25. The method of claim 24, wherein the oscillating electrical parameter has a frequency greater than 100 kHz.

26. The method of claim 21, further comprising setting the amplitude of the oscillating electrical parameter to maximize a fidelity characteristic of the blocking signal.

27. The method of claim 21, further comprising cooling the first and second electrolytes.

28. The method of claim 27, wherein the first and second electrolyte is cooled to a temperature above the freezing point of at least one of the first and second electrolytes.

29. The method of claim 21, further comprising imposing a fluid flow through the channel.

30. The method of claim 21, further comprising altering the substantially constant electric field to control the motion of the polymer through the channel.

31. The method of claim 30, wherein the substantially constant electric field is held at a high value to facilitate entry of the polymer into the channel, and is then reduced to slow a translocation velocity of the polymer.

32. The method of claim 30, further comprising controlling the motion of the polymer through the channel such that a given section of the polymer moves repeatedly back and forth through the channel.

33. The method of claim 32, wherein the given section of the polymer constitutes the entire polymer.

34. The method of claim 21, further comprising interpreting the measured signal utilizing analytical or iterative deconvolution techniques.

35. The method of claim 34, wherein the analytical or iterative deconvolution techniques are derived from measurements of the electrolytic sensing system applied to polymers of specific composition.

36. The method of claim 21, further comprising setting an amplitude and a frequency of the oscillating electric parameter such that the polymer moves less than a single monomer during a cycle of the oscillating electric parameter.

37. The method of claim 34, further comprising:
- setting an amplitude and a frequency of the oscillating electrical parameter such that the polymer moves more than a single monomer during a cycle of the oscillating electric field, and
- extracting individual monomer data from the interpreted measured signal.

38. The method of claim 34, wherein interpreting the measured signal utilizes an iterative deconvolution technique comprises the steps of:
a. choosing an initial estimate of the polymer sequence;
b. adjusting the measured signal for each polymer position utilizing the initial estimate to account for contributions to the signal of monomers that are spread throughout the channel and to develop adjusted signal values;
c. calculating an updated estimate of the polymer sequence based on the adjusted signal values; and
d. repeating steps b and c until optimum updated signal values are obtained.

39. The method of claim 21, wherein the substantially constant electric field across the channel utilizing the DC source is lower than the oscillating electrical parameter applied across the channel utilizing the AC source.

40. The method of claim 39, wherein applying the substantially constant electric field across the channel utilizing the DC source comprises applying a DC voltage; and applying the oscillating electrical parameter across the channel utilizing the AC source comprises applying an AC voltage, with the AC voltage being at least five times the DC voltage.

* * * * *